(12) United States Patent
Baru et al.

(10) Patent No.: US 6,207,456 B1
(45) Date of Patent: Mar. 27, 2001

(54) NUCLEIC ACID DELIVERY VEHICLE

(75) Inventors: Moshe Baru, Pardess-Hana; Israel Nur, Rehovot, both of (IL)

(73) Assignee: Opperbas Holding B.V., Amsterdam (NL)

( * ) Notice: Subject to any disclaimer, the term of this patent is extended or adjusted under 35 U.S.C. 154(b) by 0 days.

(21) Appl. No.: 09/029,376

(22) PCT Filed: Sep. 5, 1996

(86) PCT No.: PCT/IL96/00101

§ 371 Date: May 4, 1998

§ 102(e) Date: May 4, 1998

(87) PCT Pub. No.: WO97/10851

PCT Pub. Date: Mar. 27, 1997

(30) Foreign Application Priority Data

Sep. 7, 1995 (IL) .......................................................... 1151

(51) Int. Cl.$^7$ ........................... C12N 15/64; C12N 15/11; B32B 9/02; C07K 14/11

(52) U.S. Cl. ....................... 435/458; 428/402.2; 530/300; 536/23.1; 514/44

(58) Field of Search ........................ 435/458; 428/402.2; 530/300; 536/23.1; 514/44

(56) References Cited

U.S. PATENT DOCUMENTS

| | | |
|---|---|---|
| 5,283,122 | 2/1994 | Huang et al. . |
| 5,547,932 | 8/1996 | Curiel et al. . |

FOREIGN PATENT DOCUMENTS

| | | |
|---|---|---|
| WO 91/06309 | 5/1991 | (WO) . |
| WO 95/21259 | 8/1995 | (WO) . |

OTHER PUBLICATIONS

Gregoriadis, G., Ph.D., "Preparation of Liposome" Lipsome Technology vol. I, CRC Press, Inc., Boca Raton, FL, 1984, pp. 19–27.

Zhu, N. et al., Systemic Gene Expression After Intravenous DNA Delivery into Adult Mice, Science, vol. 261, 1993, pp. 206–211.

Wu, G.Y., et al., Receptor–Mediated Gene Delivery and Expression In Vivo*, The Journal of Biological Chemistry, vol. 263, No. 29, 1988, pp. 14621–14624.

Perales, J.C., et al., Gene Transfer In Vivo: Sustained Expression and Regulation Genes Introduced Into the Liver by Receptor–Targeted Uptake, Proc. Natl. Acad. Sci. USA, vol. 91, 1994, pp. 4086–4090.

Nicolau, C., et al., In Vivo Expression of Rat Insulin After Intravenous Administration of The Liposome–Entrapped Gene for Rat Insulin I, Proc. Natl. Acad. Sci. USA, vol. 80, 1983, pp. 1068–1072.

Leibiger, B., et al., Expression of Exogenous DNA in Rat Liver Vells After Liposome–Mediated Transfection In Vivo, Biochemical and Biophysical Research Communications, vol. 174, No. 3, 1991, pp. 1223–1231.

Cudd, A., et al., Intracellular Fate of Liposome–Encapsulated DNA in Mouse Liver. Analysis Using Electon Microscope Autoradiography and Subcellular Fractionation, Biochimica et Biophysica Acta, 845, 1985, pp. 477–491.

Curiel, D.T., et al., Adenovirus Enhancement of Transferring–Polylysine–Mediated Gene Delivery, Proc. Natl. Acad. Sci. USA, vol. 88, 1991, pp. 8850–8854.

Wagner, E., et al., Influenza Virus Hemagglutinin HA–2 N–Terminal Fusogenic Peptides Augment Gene Transfer By Transferrin–Polylysine–DNA Complexes: Toward a Synthetic Virus–Like Gene–Transfer Vehicle, Proc. Natl. Acad. Sci. USA, vol. 89, 1992, pp. 7934–7938.

Kamata, H., et al., Amphiphilic Peptides Enhance The Efficiency of Liposome–Mediated DNA Transfection, Nucleic Acids Research, vol. 22, No. 3, 1994, pp. 536–537.

Kaneda, Y., et al., The Improved Efficient Method for Introducing Macromolecules Into Cells Using HVJ (Sendai Virus) Liposomes with Ganglioside, Experimental Cell Research, 173, 1987, pp. 56–69.

Lapidot, M., et al., Fusion–Mediated Microinjection of Liposome–Enclosed DNA Into Cultured Cells with the Aid of Influenza Virus Glycoproteins, Experimental Cell Research, 189, 1990, pp. 241–246.

Tikchonenko, T.I., et al., Transfer of Condensed Viral DNA Into Eukaryotic Cells Using Proteoliposomes, Gene, 63, 1988, pp. 321–330.

Gould–Fogerite, S., et al., Chimerasome–Mediated Gene Transfer In Vitro and In Vivo, Gene, 84, 1989, pp. 429–438.

Plank, C., et al., The Influence of Endosome–Disruptive Peptides on Gene Transfer Using Synthetic Virus–Like Gene Transfer System*, The Journal of Biological Chemistry, vol. 269, No. 17, 1994, pp. 12918–12924.

Gerrard, A.J., et al., Towards Gene Therapy for Haemophilia B Using Primary Human Keratinocytes, Nature Genetics, vol. 3, 1993, pp. 180–183.

Mannino, R.J., et al., Liposome Mediated Gene Transfer, Biotechniques, vol. 6, No. 7, 1988, pp. 682–690.

*Primary Examiner*—John S. Brusca
(74) *Attorney, Agent, or Firm*—Oliff & Berridge, PLC

(57) ABSTRACT

A composition includes a liposome which has a polynucleic acid and a peptide capable of disrupting membranes under acidic conditions encapsulated within it. The composition is used for efficient transfer of nucleic acids into cells both in vitro as well as in vivo.

6 Claims, 1 Drawing Sheet

SEQUENCE LISTING

```
<160> NUMBER OF SEQ ID NOS: 4

<210> SEQ ID NO 1
<211> LENGTH: 22
<212> TYPE: PRT
<213> ORGANISM: Unknown
<220> FEATURE:
<223> OTHER INFORMATION: Description of Unknown Organism: derived from
      the Influenza virus hemagglutinin protein

<400> SEQUENCE: 1

Gly Leu Phe Glu Ala Ile Ala Gly Phe Ile Glu Asn Gly Trp Glu Gly
 1               5                  10                  15

Met Ile Asp Gly Gly Gly
            20

<210> SEQ ID NO 2
<211> LENGTH: 23
<212> TYPE: PRT
<213> ORGANISM: Unknown
<220> FEATURE:
<223> OTHER INFORMATION: Description of Unknown Organism: derived from
      the Influenza virus hemagglutinin protein

<400> SEQUENCE: 2

Gly Leu Phe Glu Ala Ile Glu Gly Phe Ile Glu Asn Gly Trp Glu Gly
 1               5                  10                  15

Met Ile Asp Gly Trp Tyr Gly
            20

<210> SEQ ID NO 3
```

```
-continued

<211> LENGTH: 23
<212> TYPE: PRT
<213> ORGANISM: Unknown
<220> FEATURE:
<223> OTHER INFORMATION: Description of Unknown Organism:derived from
      the Influenza virus hemagglutinin protein

<400> SEQUENCE: 3

Phe Leu Gly Ile Ala Glu Trp Ile Asp Ile Gly Asn Gly Trp Glu Gly
 1               5                  10                  15

Met Glu Phe Tyr Gly Glu Gly
             20

<210> SEQ ID NO 4
<211> LENGTH: 20
<212> TYPE: PRT
<213> ORGANISM: Unknown
<220> FEATURE:
<223> OTHER INFORMATION: Description of Unknown Organism: derived from
      the Influenza virus hemagglutinin protein

<400> SEQUENCE: 4

Gly Leu Phe Glu Ala Ile Ala Gly Phe Ile Glu Asn Gly Trp Glu Gly
 1               5                  10                  15

Met Ile Asp Gly
             20
```

NUCLEIC ACID DELIVERY VEHICLE

FIELD OF THE INVENTION

The present invention is generally in the field of gene delivery and concerns a delivery vehicle for delivery of nucleic acid molecules to cells, both in vivo and ex vivo.

BACKGROUND OF THE INVENTION

The development of gene therapy for inherited or acquired diseases is dependent on the establishment of safe and efficient gene delivery systems. One method for in vivo gene transfer uses viruses to transfer the exogenous gene into cells, but this method also transfers viral genes into the cells which may produce undesirable effects. In addition, contamination by wild type viruses is also a risk in this method.

Another method for in vivo gene transfer uses a complex of positively charged liposomes (composed of synthetic lipids) that bind to the DNA (the DNA is not encapsulated in the liposomes) (Zhu, N., et al., *Science*, 261:209–211, 1993). However, the toxicity of positively charged liposomes (Raz, E., et al., In: *Vaccines*, Cold Spring Harbor Laboratory Press. Cold Spring Harbor, N.Y., 1994) limits the use of this method.

A complex of poly-L-lysine coupled to DNA and a ligand which can be targeted to the cell surface was also used for in vivo gene transfer (Wu, G. Y. and Wu, C. H., *J. Biol. Chem.*, 263:14621–14624, 1988; Perales, J. C., et al., *Proc. Natl. Acad. Sci.*, USA 91:4086–4090, 1994). However, transient expression of the transferred gene and immunogenicity of the complex limits the use of this method. Neutral or negatively charged liposomes (composed of synthetic or natural lipids) that encapsulate DNA were hitherto used for in vivo gene transfer (Nicolau, C., et al., *Proc. Natl. Acad. Sci.*, USA, 80:1060–1072, 1983; Liebiger, B., et al., *Biochem. Biophys. Res. Commun.*, 174:1223–1231, 1991).

Such liposomes are non-toxic, non-immunogenic and biode-gradable (Storm et al. In: Gregoriadis, G. (Ed), *Liposome Technology*, 2nd Ed. CRC Press, Baca Rator, Fla. 1993, 00.345–383) and are therefore good candidates for repetitive high dose treatment. However, the gene transfer efficiency in these experiments was low. One possible explanation for the low efficiency is that the DNA, which is encapsulated in liposomes and enters the cytoplasm through the lysosome (Cudd, A., and Nicolau, C., *Biochim. Biophys. Acta*, 845:477–491, 1985), is degraded by active DNases in the lysosome.

Therefore, treatments that inhibit lysosome activities can increase the amount of liposome-encapsulated DNA inside the cells.

Indeed, adenovirus particle and peptides derived from the N-terminal of the Influenza virus hemagglutinin subunit HA-2, which can disrupt membrane at low pH and therefore disrupt the lysosome membrane, were shown to enhance in vitro gene transfer efficiency when coupled to poly-L-lysine and DNA (Curiel, D. T., et al., *Proc. Natl. Acad. Sci.*, USA, 88:8850–8854, 1993: Wagner, E., et al., *Proc. Natl. Acad. Sci.*, USA, 89:7934–7938, 1992).

The efficiency of cationic-liposome mediated in vitro DNA transfection into cells was also shown to be increased when the cationic-liposomes were mixed with the DNA to be transfected together with two additional peptides derived from the Influenza virus hemagglutinin protein to form a complex between these three components (Kamata, H. et al. Nuclear Acid Research 22:536–537, 1994).

Fusion of liposomes prepared by reverse-phase evaporation (RPE) carrying DNA or protein molecules to target cells was shown to be mediated by Sendai virus proteins (Kameda, Y. et al, *Exp. Cell Res.* 173:56, 1987) or influenza virus proteins (Lapidot, M., Loyter, A., *Exp. Cell Res.* 189:241–246, 1990; Tikchonenko, T. I. et al, *Gene* 63:321–330, 1988) which were introduced into the liposome membrane (i,e, were present on the liposome's outer surface). The introduction of the DNA or protein encapsulated in the liposome was dependent on the presence of an active viral fusion protein and, therefore, either intact Sendai or influenza virus particles or their reconstituted envelopes were required. Liposomes containing modified reconstituted viral envelopes integrated in their lipid bilayer (Gould-Fogerite, S. et al, *Gene*, 84, 429–438, 1989) were also prepared by the protein-cochleate technique. Such liposomes were used for stable gene transfer and expression in animals.

All the above mentioned liposomes have large viral particles or reconstituted viral envelopes integrated in their lipid membrane which protrude outwards from the liposome membrane. In vivo administration of liposomes carrying such large viral particles may be hindered by the high antigenicity of such large particles as well as occasionally by their toxic effects.

SUMMARY OF THE INVENTION

It is the object of the present invention to provide a novel polynucleic acid delivery system.

It is a further object of the invention to provide a method for the introduction of a polynucleic acid sequences into cells.

The invention concerns a novel composition for liposome-mediated ex vivo (particularly to cells removed from the body and returned to the body following a genetic manipulation) and in vivo transfer of nucleic acid sequences to cells. The formulation comprises liposomes in which a nucleic acid sequence is co-capsulated with a short peptide that disrupts membranes at a low pH.

The present invention thus provides a composition comprising:

i. a polynucleic acid molecule;
  ii. a liposome; and
  iii. a peptide comprised of less than about 50 amino acids which disrupts membranes under acidic conditions;
  said peptide and the polynucleic acid molecule being encapsulated within the liposome.

The polynucleic acid molecule may be a DNA molecule, an RNA molecule, a moleclue consisting of both ribonucleotides and deoxy-nucleotides (RNA/DNA hybrid). The polynucleic acid molecule may be a large nucleic acid construct, such as a plasmid, an oligonucleotide, etc. The polynucleic acid is typically encapsulated within the aqueous interior of the liposome.

The liposomes used in accordance with the invention may be multilamellar or unilamellars. Most types of liposomes belong to either one of the following three types: multilamellar vesicles (MLV), small unilamellar vesicles (SUV) and large unilamellar vesicles (LUV). MLVs typically form spontaneously upon hydration of dried phospholipids. SUVs, may be formed from MLVs by sonication and unlike the multilayered, onion skin-like structure of MLVs, they are single layered. SUVs are small with a high surface-to-volume ratio and thus have the lowest capture volume of aqueous space per weight of lipid.

As distinct from SUVs, LUVs have a large aqueous compartment and a single, or at times a few, lipid layers.

The liposomes may be comprised of a variety of lipids, including phospholipids, glycolipids, etc. Preferably phospholipids constitute a major component in the liposomes' membranes. Preferred phospholipids are α-lecithines (also known as phosphatidyl-cholines), which are mixtures of diglyceride of stearic, palmitic and oleic acids linked to the choline ester of phosphoric acid. Lecithines are found in and obtainable from animals and plants. Preferred sources of lecithines are eggs, soybeans, animal tissues such as brain, heart, and the like. Lecithines can also be produced synthetically. As will no doubt be appreciated by the artisan, the source of the phospholipid is immaterial to the present invention and any phospholipid will likely be suitable.

Examples of specific phosphatides are L-α-(distearoyl) lecithin, L-α(diapalmitoyl) lecithin, L-α-phosphatide acid, L-α-(dilauroyl)-phosphatidic acid, L-α-(dimyristoyl) phosphatidic acid, L-α-(dioleoyl) phosphatidic acid, DL-α-(dipalmitoyl) phosphatidic acid, L-α-(distearoyl) phosphatidic acid, and the various types of L-α-phosphatidylcholines prepared from brain, liver, egg yolk, heart, soybean and the like, or synthetically, and salts thereof. Other suitable modifications include the controlled peroxidation of the fatty acyl residue cross-linkers in the phosphatidylcholines (PC) and the zwitterionic amphiphates which form micelles by themselves or when mixed with the PCs such as alkyl analogues of PC.

In addition to phospholipids, the liposomes may also comprise various other lipophilic or amphophilic molecules. The composition of the lipid membrane may be tailored for a variety of specific uses, either to obtain certain stability, size distribution, etc.

In the composition of the invention, the lipids and the other lipophilic or amphophilic molecules constitute together about 1–30% of the composition's volume, preferably about 10%. In addition to the composition's ingredients, mentioned above, the composition may also comprise various preservatives and antioxidants.

The compositions of the inventions are preferably dehydrated, rehydrated vesicles (DRV). DRVs are prepared by rehydration of a dehydrated composition which upon addition of water spontaneously forms the composition of the invention. DRVs may be prepared in a number of ways. By one exemplary way, a mixture is first prepared consisting of SUVs, said agent, the polynucleic acid molecule and cryoprotectants. Examples of cryoprotectants are sucrose and amino acid (e.g. hystidine, lysine and arginine). The cryoprotectants are typically added at an osmolarity which is less than physiological (i.e. less than about 300 mOsm). The mixture is then lyophilized up to a water content of less than 2%. The reconstitution is typically a multi-stage procedure wherein the first step is a low volume rehydration, i.e., rehydration with a volume of an aqueous solution (which may be water or preferably an aqueous solution comprising salts (e.g. NaCl) or other solutes (e.g. sugar) to yield isotonicity with body fluids, i.e. osmolarity of about 300 mOsm), equal to about a third or less than the final water volume. Typically, as noted above, the compositions of the invention comprises, on a weight per volume basis, about 10% lipids and a low volume of the aqueous solution in the first hydration step, is typically addition of water to yield a concentration of lipids of about 30% (w/v). Then aqueous solution is further added gradually to yield the final volume.

In another exemplary way, DRVs can be prepared by mixing the ingredients of the composition with a tertiary alcohol (e.g. tert-butanol)-in-water solution, with the alcohol concentration being in the range of about 10–30%. The concentration of the alcohol typically correlates the hydrophobicity of the lipid ingredients, with higher hydrophobicity meaning a higher alcohol concentration. The mixture is then lyophilized (alcohol is more volatile than water and accordingly lyophilization is more rapid than that achieved with a solution comprising water alone). The rehydration is performed in a similar manner to that described above.

The manner of preparation of liposomes and their tailoring to suit a specific need is generally known to the artisan and is outside the scope of the present writing. Non-limiting examples of methods for the preparation of liposomes are those mentioned above being reverse-phase evaporation (RPE) (Kameda et al, supra) or the protein-cochleate technique (Gould-Fagerite et al, supra).

The liposome of the invention may be targeted to a desired cell by various targeting methods known per se, such as by having a recognition molecule anchored in the liposome membrane, e.g. a member of a binding couple, the other member being one molecule on the surface of the target cell (examples of such binding couples are antibody-antigen, the antibody being anchored within the cell, and the antigen being antigen specifying the target cell; ligand-receptor couple, ligand being anchored in the liposome membrane and the receptor being a specific receptor for the target cell; sugar-lectin couple, the lectin being anchored in the cell membrane and the sugar being displayed on a cell surface; etc.).

The peptide comprised in the composition of the invention is a small molecule comprising up to about 50 amino acids (a.a.). In contrast to prior art liposomes which incorporate large viral particles in their membrane having at least a portion protruding outwards from the liposome surface, the peptide of the present invention is encapsulated within the liposome wherein it is either incorporated within the lipid layer of the liposome or is encapsulated in the liposomes inner aqueous part. Therefore, in vivo administration of a composition comprising a liposome of the invention does not elicit an immunogenic reaction and the composition also has no toxic effects.

The peptide of the invention is such which changes its conformation under acidic conditions to conformation where it becomes active in disrupting membranes. Such a peptide typically undergoes a conformational change under acidic conditions to a conformation of an α-helix where it becomes membrane disruptive. A liposome is internalized into a cell by endocytosis, and eventually reaches the lysosome within the cell. Owing to the acidic conditions within the lysosome, the peptide becomes membrane disruptive and following disruption of the lysosome's membrane the DNA is released into the cytoplasm.

Examples of such peptides include peptides such as those described by Plank et al. *J. Biol. Chem.,* 269:12918–12924, 1994) a variety of virus-derived peptides having this property, such as the influenza virus hemagglutinin HA-2 N-terminal physiogenic peptides (Wagner et al, supra) or Sendai virus derived particles (Kameda et al, supra). Other peptides may also be derived from various bacteria or alternatively may be one synthezied by chemical or recombinant genetic engineering methods. It will be appreciated that these are but an example and there are a variety of other peptides which can be used for this purpose.

The invention also provides a method for introducing nucleic acid molecules to cells comprising:

(a) encapsulating a nucleic acid molecule within a liposome together with a peptide capable of disrupting membranes under acidic conditions; said peptide being comprised of less than about 50 amino acids; and (b) delivering said liposome to the cells.

A specific embodiment in accordance with the invention is the in vivo delivery of polynucleic acid molecules to liver cells. For in vivo delivery of the polynucleic acid molecules, the compositions may be injected intravenously or intra peritoneally.

The invention will now be illustrated in the following non-limiting specific embodiment.

DESCRIPTION OF SPECIFIC EMBODIMENTS

Figure 1:
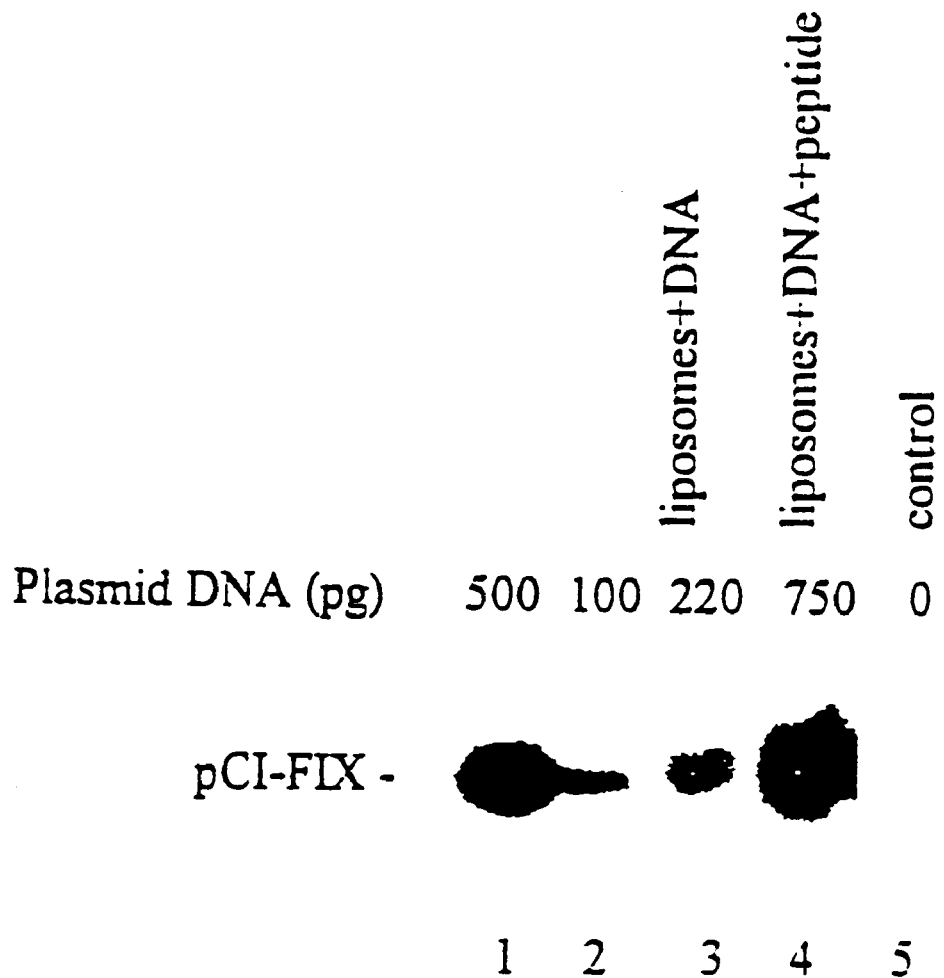
FIG. 1 shows results of an experiment demonstrating the presence of plasmid DNA in mouse liver 7 days post-injection of liposome encapsulated plasmid DNA. Balb/c mice (8 weeks old) were injected i.v. through the tail vein with 500 μg of factor IX expression vector (pCI-FIX) encapsulated in liposome with (lane 4) or without (lane 3) a 22 mer peptide. Total DNA (30 μg) purified from livers that were excised 7 days after the injection or from untreated mouse (lane 5), were digested with BamHI loaded on a 1% agarose gel and subjected to Southern blot analysis probed with $^{32}P$ random priming-labelled Bluescript plasmid DNA. The number above each lane indicated the amount of plasmid DNA calculated according to 500, and 10 pg of the plasmid pCI-FIX (lane 1 and 2) loaded on the same gel.

1. Encapsulation of membrane disrupting peptide in liposomes

A 22 mer peptide, including 20 amino acids derived from the N-terminal sequence of the Influenza virus Hemagglutinin subunit HA-2, was synthesized by the Fmoc procedure using an Applied Biosystem 430A peptide synthesizer. The peptide had the following sequence (the first 20 amino acid residues are those of the Influenza virus Hemagglutinin protein with a substitution of glycine for glutamic acid at position 4):

Gly-Leu-Phe-Glu-Ala-Ile-Ala-Gly-Phe-Ile-Glu-Asn-Gly-Trp-Glu-Gly-Met-Ile-Asp-Gly-Gly-Gly. (SEQ ID NO:1)

In addition, palmitic acid was covalently bound to the N-terminal of an aliquot of the synthesized peptide.

The free peptide and the peptide attached to palmitic acid were encapsulated in liposomes composed of egg phosphatidylcholine (EPC) by the freeze-drying method (Kirby and Gregoriadis in: *Gregoriadis, G(Ed) Liposome Technology*, CRC Press, Boca Raton, Fla., 1984, pp.19–24): EPC supplemented with 0.11% (molar ratio) DL-α-tocopherol (Lipoid) was dissolved to 20% (w/v) in tert-butanol and lyophilized. The dry lipid was resuspended to 10% (w/v)) in $H_2O$ and homogenized, first in a high-shear mixer (Kinematica) and then in a high-pressure homogenizer (Rannie). The resulting solution contained small unilamellar vesicles (SUV), 30–50 nm in size as measured by particle analyzer (Counter Electronics). The free peptide or the peptide attached to palmitic acid was dissolved in 50 mM $NaHCO_3$ and mixed with the SUV suspension at a ratio of either 1 or 2.5% molar ratio of peptide to lipid. The mixture was shell-frozen to a thin layer in siliconized glass vials in a dry ice/ethanol bath and lyophilized. Before use, the dry lipids and peptide were hydrated in two stages. First, $H_2O$ was added to 30% of the final volume and the mixture was shaken until a homogeneous solution was obtained. The solution was then adjusted to 10% (w/v) lipid and 155 mM NaCl. Following hydration, a portion of the liposome solution was centrifuged at 15,000×g for 10 min. at 4° C., and the supernatant containing free peptide was separated from the liposome pellet. The pelleted liposomes were then washed with 2 volumes of 155 mM NaCl and centrifuged as above. The peptide content in each fraction was determined by measuring adsorption of the peptide at 280 nm and then percentage of encapsulation was calculated. The results are summarized below in Table I.

TABLE I

| Peptide type and concentration (molar ratio of peptide to lipid) | % encapsulation |
| --- | --- |
| 1% mole of free peptide | 100 |
| 2.5% mole of free peptide | 57 |
| 1% mole of palmitic acid-peptide | 75 |
| 2.5% mole of palmitic acid-peptide | 20 |

These results indicate that encapsulation of the 22 mer peptide in liposomes is the highest at a 1% molar ratio of peptide to lipids, and that a higher molar ratio results in lower encapsulation level. In addition, free peptide was encapsulated more efficiently than peptide attached to palmitic acid.

2. Co-encapsulation of DNA and peptide in EPC liposomes

Three hundred and fifty micrograms of factor IX expression vector pCI-FIX (EcoRI-BamHI fragment of the plasmid pLIXSNL-2 (Gerrard et al., *Nature Genetic* 3:180–183 (1993) containing human factor IX cDNA inserted into the EcoRI and BamHI sites of the expression vector pCI (Promega, USA)) was mixed with 10 ng of nick translated factor IX expression vector labeled with α-$^{32}P$ dATP. The DNA mixture was then mixed with 0.56 ml of 5% SUV of EPC and 0.83 mg of peptide (1% molar ratio of peptide to lipid) dissolved in 50 mM $NaHCO_3$. The final mixture was shell freezed and liposomes were prepared as described in Section 2. Following hydration, a portion of the liposome solution was centrifuged at 15,000×g for 10 mins. at 4° C., and the supernatant containing free DNA was separated from the liposome pellet. The pelleted liposomes were then washed with 2 volumes of 155 mM NaCl and centrifuged as above. The DNA content in each fraction was determined using a β counter. Percentages of DNA associated with liposome were calculated by dividing $^{32}P$ counts in the washed liposome pellet by total $^{32}P$ counts in the initial liposome solution. The peptide content in each fraction was determined by dissolving 100 μl sample of fraction in 50 nM $NaHCO_3$ and 5.1% (v/v) reduced triton x-100 (Sigma), and measuring fluorescence of the peptide (excitation at 280 nm and emission at 340 nm) using a spectrofluorimeter machine (LS 50B, Parkin, Elmer, USA). Percentages of peptide associated with liposomes were calculated by dividing peptide fluorescention level in the washed liposome pellet by peptide fluorescention level in the initial liposome solution. The results are shown in Table II. It can be seen that 48% of the DNA was associated with liposomes which co-encapsulate peptide. This result is indication that encapsulation of the peptide in the liposomes has no significant effect on encapsulation of DNA in the same liposomes.

TABLE II

Co-encapsulation of DNA and peptide in EPC liposomes

| Type of liposome formulation | Percentage of liposome-associated DNA | Percentage of liposome-associated peptide |
| --- | --- | --- |
| Liposomes and DNA | 48 | — |
| Liposomes, DNA and peptide | 42 | 63 |

3. In-vivo gene transfer by a liposome formulation containing factor IX expression vector The liposome formulations were prepared as described in Sections 2 and 3. The first formulation contains 1.5 mg of human factor IX expression vector and 120 mg of EPC. The second formulation contains 1.5 mg of factor IX expression vector, 120 mg of EPC and 3.5 mg of the peptide. After the hydration, the liposomes were injected i.v. into 8 weeks old male Balb/c mice (each formulation was injected into 3 mice). At 7 days post-injection the mice were sacrificed and DNA was purified from the livers of the mice. (The liver was the organ which adsorbed most of this kind of liposome following i.v. injection).

Total DNA (50 µg) was extracted from the liver of liposome-injected mice and was used to transform competent E.coli (JM109) as described in Sambrook et al. (Molecular Cloning, A Laboratory Manual, 2nd ed., Cold Spring Harbor Laboratory Press, Cold Spring Harbor, N.Y. 1989). The transformed bacteria were plated on Luria-Bertani (medium) (LB) agar plates supplemented with 100 µg Ap/ml, grown overnight at 37° C. and $Ap^R$ colonies were scored. Transformation efficiency and quantitation of plasmid DNA in the liver DNA was determined using a standard curve developed by transformation of competent bacteria with 500, 100 and 10 pg of factor IX expression vector mixed with 50 µg of liver DNA from untreated mice. The transformation efficiency was $5 \times 10^5$ colonies/µg of purified plasmid DNA. Because only the injected factor IX expression vector could confer Ap resistance, the number of transformed Ap resistant ($Ap^R$) bacterial colonies was a direct indication of the plasmid DNA content within the total mouse liver DNA. As indicated in Table III, colonies of $Ap^R$ bacteria were found only in plates containing bacteria which had been transformed with DNA purified from livers of mice that had been injected with liposome-encapsulated factor IX expression plasmid. The number of $Ap^R$ bacterial colonies in plates of bacteria that were transformed with DNA purified from mice livers that were injected with the formulation containing DNA lipids and peptide was 2.2 higher than the number of $Ap^R$ bacterial colonies in plates of bacteria that were transformed with DNA purified from livers of mice that were injected with the formulation containing only lipid and DNA.

TABLE III

Bacterial transformation by total DNA purified from livers of mice injected with liposome-encapsulated plasmid DNA

| Injected formulation | pg plasmid DNA/ 50 µg liver DNA average ± SD (n = 3) |
| --- | --- |
| liposomes + plasmid DNA | 53 ± 13 |
| liposomes + plasmid DNA + peptide | 117 ± 31 |
| untreated mice | 0 |

Another quantitative measurement of the amount of factor IX expression vector in total cellular DNA purified from mice livers was done by Southern blot analysis. By comparing lanes 3 and 4 in FIG. 1, it can be seen that the amount of injected plasmid DNA was 3.4 times higher in mice that were injected with the formulation containing the peptide than in mice that were injected with the formulation which does not contain the peptide. These results are in agreement with the bacteria transformation results, and indicate that the gene transfer efficiency is significantly increased when the membrane disrupting peptide is included in the liposome formulation.

4. Factor IX synthesis in mice injected with liposome formulations containing human factor IX expression vector The liposome formulations that were described in Section 4 were injected i.v. into 2 groups of Balb/c mice (3 mice in each group). Four days post injection the mice were bled, plasma samples were prepared and tested by human factor IX specific ELISA. The plasma samples were analyzed for human FIX by ELISA using two anti-human FIX monoclonal Ab (HIX-1 and HIX-5, Sigma) as primary Ab, and rabbit anti-human FIX (Stago) as a secondary Ab. Bound rabbit Ab were detected with alkaline phosphatase conjugated anti-rabbit IgG monoclonal Ab (Sigma) and p-nitrophenyl phosphate (Sigma). Normal pooled human plasma (Stago) was used to plot a calibration curve of human FIX antigen (normal level=5 µg/ml human plasma). This assay can detect as little as 10 pg human FIX in mouse plasma.

As can be seen in Table IV, significant levels of human factor IX protein were detected in the plasma of mice that had been injected with the liposome formulations containing human factor IX expression vector. The amount of human factor IX in the blood of mice that were injected with the liposome formulation containing the membrane disrupting peptide was 2.1 higher than the amount of human factor IX in the blood of mice that were injected with liposome formulation that did not contain the peptide.

TABLE IV

Human factor IX in mouse plasma

| Injected formulation | pg hFIX/ml mouse plasma average ± SD (n = 2) |
| --- | --- |
| Factor IX expression vector encapsulated in liposomes | 45 ± 1.5 |
| Factor IX expression vector and membrane disrupting peptide encapsulated in liposomes | 97 ± 4.5 |
| Untreated mice | 0 |

5. Production of factor VIII (FVIII) in mice injected with liposome formulations containing a human factor VIII expression vector Three liposome formulations were prepared as described in sections 2 and 3 above. The first formulation contained 1.5 mg of human factor VIII expression vector pCI-FVIII [pCI vector (Promega) containing FVIII cDNA which encodes FVIII protein with a deletion of 695 amino acids of its B domain] and 150 mg of EPC. The second formulation contained 1.5 mg of the expression vector pCI-FVIII, 150 mg of EPC and 5.2 mg of a lysosome disrupting peptide which is derived from the Influenza virus hemagglutinin protein and which increased the transfection efficiency of a complex of DNA and polylysine into cells in vitro (Plank, C., et al., J. Biol. Chem. 269:12918–12924, 1994) and has the following amino acid sequence:

Gly-Leu-Phe-Glu-Ala-Ile-Glu-Gly-Phe-Ile-Glu-Asn-Gly-Trp-Glu-Gly-Met-Ile-Asp-Gly-Trp-Tyr-Gly. (SEQ ID NO:2)

The third formulation contained 1.5 mg of the factor VIII expression vector pCI-FVIII, 150 mg of EPC and 5.2 mg of a control peptide which contains the same amino acids as the peptide described above but in a scrambled order (hereinafter "scrambled peptide"):

Phe-Leu-Gly-lle-Ala-Glu-Trp-Ile-Asp-Ile-Gly-Asn-Gly-Trp-Gly-Gly-Met-Glu-Phe-Tyr-Gly-Glu-Gly. (SEQ ID NO:3)

The liposome formulations were injected i.v. into 6 week-old male Balb/c mice (each formulation was injected into 3 mice). As control, mice were injected with empty liposomes and a liposome-encapsulated pCI vector. At five days post-injection the mice were bled and plasma samples were prepared. Factor VIII activity in the mouse plasma was measured by a chromogenic assay (Baxter), and the level of human factor VIII in the mouse plasma was calculated as FVIII activity in the plasma of liposome-injected mice less the activity in the plasma of untreated mice.

As seen in Table V below, co-encapsulation of lysosome disrupting peptide with the expression vector in the liposomes significantly increased factor VIII production in mice. The control scrambled peptide, had no effect on factor VIII production.

TABLE V

Factor VIII activity in mouse plasma 3 days post-injection of liposome formulations containing a factor VIII expression vector

| Injected formulation | Average factor VIII activity above base level (u/ml) (n = 3) | ng human factor VIII/ml mouse plasma[1] |
|---|---|---|
| Untreated mice | 0 | 0 |
| Empty liposomes | 0 | 0 |
| Liposome-encapsulated control DNA | 0 | 0 |
| Liposome encapsulated factor VIII expression vector | 0.38 | 38–76 |
| Liposome encapsulated factor VIII expression vector and lysosome disrupting peptide | 1.08 | 108–216 |
| Liposome encapsulated factor VIII expression vector and control peptide | 0.36 | 36–72 |

[1]Factor VIII amounts were calculated according to 1 unit FVIII = 100–200 ng

6. Conclusion

Enhancement of gene transfer efficiency by membrane-disrupting peptide was demonstrated in this study by results obtained through several different methods:

(a) southern blot analysis of mouse liver DNA and transfection of liver DNA into bacteria indicated that the amount of plasmid DNA absorbed by liver cells was 2.2–3.4 times higher in mice injected with liposome encapsulated DNA and peptide than in mice injected with liposomes containing only DNA (FIG. 1, Table III).

(b) human factor IX level in the mouse plasma measured by ELISA was 2.15 times higher in mice injected with liposome encapsulated FIX expression vector and peptide than in mice injected with liposomes containing only DNA (Table IV); and (c) the level of factor VIII in mouse plasma measured by a chromogenic assay was 2.8 times higher in mice injected with liposomes containing FVIII expression vector and lysosome disrupting peptide than in mice injected with liposomes containing FVIII expression vector alone or co-encapsulated with control peptide (Table V).

In addition, the fact that the "scrambled" peptide was shown to be inactive indicated that the enhancement effect mediated by the two other peptides was due to their lysosome disrupting activity.

What is claimed is:

1. A composition comprising:
   i) a polynucleic acid molecule;
   ii) a liposome; and
   iii) a peptide comprised of less than about 50 amino acids which disrupts membranes under acidic conditions;
   said peptide and the polynucleic acid molecule being encapsulated within the liposome, wherein said peptide is derived from an influenza virus protein and said peptide comprises SEQ ID NO:4.

2. A composition comprising:
   i) a polynucleic acid molecule;
   ii) a liposome; and
   iii) a peptide comprised of less than about 50 amino acids which disrupts membranes under acidic conditions;
   said peptide and the polynucleic acid molecule being encapsulated within the liposome, wherein said peptide is derived from an influenza virus protein and said peptide comprises SEQ ID NO:1.

3. A method of introducing nucleic acid molecules to cells comprising:

(a) encapsulating a nucleic acid molecule with a liposome together with a peptide capable of disrupting membranes under acidic conditions, said peptide being comprised of less than about 50 amino acids, wherein said peptide comprises SEQ ID NO:4; and
   (b) delivering said liposomes to the cells.

4. A method according to claim 3, wherein the nucleic acid molecule is delivered to cells in vivo.

5. A method of introducing nucleic acid molecules to cells comprising:

(a) encapsulating a nucleic acid molecule with a liposome together with a peptide capable of disrupting membranes under acidic conditions, said peptide being comprised of less than about 50 amino acids, wherein said peptide comprises SEQ ID NO:1; and
   delivering said liposomes to the cells.

6. A method according to claim 5, wherein the nucleic acid molecule is delivered to cells in vivo.

* * * * *